(12) United States Patent
Bodner

(10) Patent No.: US 9,352,125 B2
(45) Date of Patent: May 31, 2016

(54) PORTAL ANCHORS INCORPORATING STRAIN RELIEF CUP AND SYSTEMS USING SAME

(71) Applicant: Medtronic, Inc., Minneapolis, MN (US)

(72) Inventor: Jeffrey P. Bodner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 253 days.

(21) Appl. No.: 13/796,012

(22) Filed: Mar. 12, 2013

(65) Prior Publication Data
US 2014/0276529 A1    Sep. 18, 2014

(51) Int. Cl.
*A61M 25/02* (2006.01)

(52) U.S. Cl.
CPC .......... *A61M 25/02* (2013.01); *A61M 2025/028* (2013.01); *A61M 2025/0213* (2013.01); *A61M 2025/0293* (2013.01)

(58) Field of Classification Search
CPC .......... A61M 25/02; A61M 2039/025; A61M 2039/0261; A61M 2210/0687; A61M 2025/0213; A61M 2025/028; A61M 2025/0293; A61M 25/04
USPC ........................................................ 604/174
See application file for complete search history.

(56) References Cited

U.S. PATENT DOCUMENTS

| | | | |
|---|---|---|---|
| 3,021,842 A | 2/1962 | Flood | |
| 3,262,452 A | 7/1966 | Hardy et al. | |
| 3,444,861 A | 5/1969 | Schulte | |
| 3,760,811 A | 9/1973 | Andrew | |
| 4,025,964 A | 5/1977 | Owens | |
| 4,328,813 A | 5/1982 | Ray | |
| 4,350,159 A | 9/1982 | Gouda | |
| 4,360,025 A | 11/1982 | Edwards | |
| 4,629,451 A | 12/1986 | Winters et al. | |
| 4,805,634 A | 2/1989 | Ullrich et al. | |
| 4,993,425 A | 2/1991 | Kronberg | |
| 5,263,956 A | 11/1993 | Nobles | |
| 5,464,446 A | 11/1995 | Dreessen et al. | |
| 5,540,648 A | 7/1996 | Yoon | |

(Continued)

FOREIGN PATENT DOCUMENTS

| | | |
|---|---|---|
| DE | 19726141 | 1/1999 |
| DE | 19808220 | 9/1999 |

OTHER PUBLICATIONS

"Gelfoam(r) absorbable gelatin compressed sponge, USP" datasheet [online]. Pfizer Inc, New York, NY, (c) 2002-2013 [retrieved on May 14, 2013]. Retrieved from the Internet: <URL:http://www.pfizer.com/files/products/uspi_gelfoam_plus.pdf>, 7 pages.

(Continued)

*Primary Examiner* — Kami A Bosworth
*Assistant Examiner* — Brandy S Lee
(74) *Attorney, Agent, or Firm* — Mueting, Raasch & Gebhardt, P.A.

(57) ABSTRACT

Anchors for securing a medical device relative to a burr hole, wherein the anchors may accommodate most any implantation trajectory through the burr hole. Such anchors may further secure the device along any such trajectory without imparting undesirable biasing forces that may shift the device from its intended implanted location. In some embodiments, the anchor is configured with a cup-shaped retention member through which the medical device passes. The retention member may receive a volume of curable material therein to provide strain relief to the medical device.

18 Claims, 12 Drawing Sheets

(56) References Cited

U.S. PATENT DOCUMENTS

| | | |
|---|---|---|
| 5,662,600 A | 9/1997 | Watson et al. |
| 5,713,858 A | 2/1998 | Heruth et al. |
| 5,843,150 A | 12/1998 | Dreessen et al. |
| 5,865,842 A * | 2/1999 | Knuth et al. ............... 607/116 |
| 5,916,200 A | 6/1999 | Eppley et al. |
| 5,927,277 A * | 7/1999 | Baudino et al. ............ 600/386 |
| 5,954,687 A * | 9/1999 | Baudino ...................... 604/48 |
| 6,044,304 A | 3/2000 | Baudino |
| 6,134,477 A | 10/2000 | Knuteson |
| 6,210,417 B1 | 4/2001 | Baudino et al. |
| 6,321,104 B1 | 11/2001 | Gielen et al. |
| 6,356,792 B1 | 3/2002 | Errico et al. |
| 6,482,182 B1 | 11/2002 | Carroll et al. |
| 6,609,020 B2 | 8/2003 | Gill |
| 7,004,948 B1 | 2/2006 | Pianca et al. |
| 7,454,251 B2 | 11/2008 | Rezai et al. |
| 7,553,298 B2 | 6/2009 | Hunt et al. |
| 7,580,756 B2 | 8/2009 | Schulte et al. |
| 7,636,596 B2 | 12/2009 | Solar |
| 7,637,915 B2 | 12/2009 | Parmer et al. |
| 7,704,260 B2 | 4/2010 | Skakoon et al. |
| 7,828,809 B2 | 11/2010 | Skakoon et al. |
| 7,981,119 B2 | 7/2011 | Lando et al. |
| 7,988,674 B2 | 8/2011 | Adams et al. |
| 8,075,531 B2 | 12/2011 | Davey |
| 2002/0019641 A1 | 2/2002 | Truwit |
| 2002/0052610 A1 | 5/2002 | Skakoon et al. |
| 2002/0151871 A1 | 10/2002 | Gaiser et al. |
| 2003/0040753 A1 | 2/2003 | Daum et al. |
| 2003/0199831 A1 | 10/2003 | Morris et al. |
| 2004/0034367 A1 | 2/2004 | Malinowski |
| 2004/0243146 A1 | 12/2004 | Chesbrough et al. |
| 2005/0054985 A1 | 3/2005 | Mogg |
| 2005/0125007 A1 | 6/2005 | Gill |
| 2005/0143799 A1 | 6/2005 | Black et al. |
| 2005/0143800 A1 | 6/2005 | Lando et al. |
| 2005/0192594 A1 | 9/2005 | Skakoon et al. |
| 2006/0111688 A1 | 5/2006 | Kraus et al. |
| 2006/0129126 A1 | 6/2006 | Kaplitt et al. |
| 2008/0200798 A1 | 8/2008 | Ecklund et al. |
| 2009/0187149 A1 | 7/2009 | Nelson |
| 2009/0306501 A1 | 12/2009 | Flint |
| 2010/0174240 A1 * | 7/2010 | Wells et al. ............... 604/175 |
| 2010/0217196 A1 | 8/2010 | Nelson |
| 2010/0312280 A1 | 12/2010 | Overes et al. |
| 2011/0009879 A1 * | 1/2011 | Derrick et al. ............ 606/130 |
| 2011/0270187 A1 | 11/2011 | Nelson |
| 2012/0083742 A1 | 4/2012 | Nelson |
| 2013/0096570 A1 * | 4/2013 | Solar et al. ............... 606/108 |

OTHER PUBLICATIONS

"STIMLOC by ign," datasheet, Image Guided Neurologics, Inc. (c) 2004 Image Guided Neurologics, Inc., Melbourne, FL, Retrieved from the Internet: <URL://http.www.igneurologics.com/pages/dba2/stimloc.pdf>; 2 pgs.

\* cited by examiner

PORTAL ANCHORS INCORPORATING STRAIN RELIEF CUP AND SYSTEMS USING SAME

Embodiments of the present invention relate generally to medical devices and, more particularly, to anchors for securing a therapy delivery device (e.g., a catheter or lead) within, or otherwise relative to, a body portal such as a cranial burr hole, and to systems and methods incorporating such anchors.

BACKGROUND

Medical procedures involving insertion of a medical device into the brain (through a burr hole formed in the skull) are used to treat a variety of medical conditions. For example, electrical stimulation of the brain to relieve chronic pain, or for the treatment of movement disorders, may necessitate the implantation, via the burr hole, of an electrode or lead. Similarly, burr holes are typically formed to allow implantation of a therapy catheter, e.g., an intraparenchymal (IPA) or intracerebroventricular catheter, to treat various ailments.

Use of such devices to deliver therapy to the brain generally involves the insertion of the device into the brain and positioning a distal, therapy delivery tip of the device at a desired target tissue location. During a typical implantation procedure, an incision is made in the scalp to expose the patient's skull. After forming a burr hole through the skull, the device is inserted into the brain. To accurately place the device, surgeons typically use stereotactic apparatus/procedures. One exemplary stereotactic apparatus is described in U.S. Pat. No. 4,350,159 to Gouda, which may be used to position, for example, an electrode.

As one can appreciate, once an inserted device such as a catheter is properly positioned, it is important that it be adequately immobilized to prevent movement of the distal tip from the intended location. Even minimal movement of the device tip may reduce therapeutic efficacy. Accordingly, reliable methods and apparatus for anchoring and securing the device relative to the burr hole are desirable.

After locating the distal tip at the target tissue location, a portion of the medical device that extends outside of the burr hole may be anchored using an anchor device. A protruding, proximal end of the medical device may then connect to a therapeutic source (e.g., for a catheter, to a reservoir containing a therapeutic agent; for a lead, to an electrical stimulation source). For example, when the medical device is a therapy catheter, the proximal end of the therapy catheter may be bent (e.g., at about 90 degrees) to connect to a second, delivery or pump catheter that is, in turn, coupled to an implantable infusion pump containing the therapeutic agent. As a result, the agent may be delivered through the delivery catheter and the therapy catheter to the desired target tissue location within the patient.

While effective, such a surgical procedure may present drawbacks. For example, the catheter may store energy in the vicinity of the bend. As the medical device seeks to unload this stored energy, migration of the therapy delivery tip from its target tissue location may result. Additionally, surgeons increasingly desire access to the brain via device trajectories that are angled relative to the burr hole. That is, some surgeries may benefit from insertion of the medical device into the brain at an angle that is canted from (e.g., not aligned with) an axis normal to the skull surface at the burr hole. Many existing burr hole anchors, however, are configured to grip or secure the medical device assuming that its orientation is normal to the skull surface. In the case of an angled implant trajectory, such anchors may impart clamping forces that can bias the device away from its original implant trajectory, and thus bias the therapy delivery tip away from the intended target tissue location. This result may be amplified with increased trajectory angle, stiffer medical devices, and shallower insertion depths.

SUMMARY

The present invention may overcome these and other issues by providing, in one embodiment, a cranial anchor configured to secure an elongate medical device implanted via a burr hole. The anchor may include a base configured to secure to tissue surrounding the burr hole, wherein the base includes an upper side, lower side, outer edge, and inner edge. The inner edge may define an opening passing between the upper and lower sides. A cup-shaped retention member may also be provided and includes a sidewall and a floor. The retention member may be configured to be received within the opening and secure to the base, wherein the floor is positioned at an elevation at or near the lower side of the base when the retention member is secured to the base within the opening. The floor is configured to permit passage of the medical device through the floor at any one of two or more locations, the sidewall and floor defining a receptacle configured to receive and retain a volume of curable material therein.

In another embodiment, a cranial anchor is provided and configured to secure an elongate medical device implanted via a burr hole. The anchor may include a base configured to secure to tissue surrounding the burr hole, wherein the base includes an upper side, lower side, outer edge, and inner edge. The inner edge may define an opening passing between the upper and lower sides. A cup-shaped retention member is also provided and includes a sidewall and a floor forming a partially enclosed receptacle having an open top, the receptacle configured to receive and retain a volume of curable material therein. The retention member may be configured to be removably received within the opening and secure to the base, wherein the floor comprises a membrane operable to be pierced by the medical device, or by a tool used during implantation of the medical device.

In another embodiment, a cranial anchor is provided and configured to secure an elongate medical device implanted via a burr hole. In this embodiment, the anchor may include a base configured to secure to tissue surrounding the burr hole. The base may include an upper side, lower side, outer edge, and inner edge, wherein the inner edge defines an opening passing between the upper and lower sides. A cup-shaped retention member may also be included and configured to be removably received within the opening and secure to the base. The retention member may define a floor positioned at an elevation at or near the lower side of the base when the retention member is secured to the base within the opening, the floor defining a plurality of apertures, wherein each aperture is configured to receive therein the medical device with clearance.

In yet another embodiment, an implantable therapy delivery system is provided that includes an elongate medical device configured to extend through a burr hole of a living being, wherein the medical device includes a therapy delivery tip for placement at a target tissue location within the living being. A therapy source is also provided and configured to connect to the medical device. A cranial anchor is further provided and configured to secure the medical device at or near the burr hole. The anchor may include: a base configured to secure to tissue surrounding the burr hole, the base comprising an upper side, lower side, outer edge, and inner edge, the inner edge defining an opening passing between the upper and lower sides; and a cup-shaped retention member comprising a sidewall and a floor. The retention member is configured to be received within the opening and secure to the base, the floor positioned at an elevation at or near the lower side of the base when the retention member is secured to the base within the opening. The floor is configured to permit passage of the medical device through the floor at any one of two or more locations. The sidewall and floor may define a receptacle configured to receive and retain a volume of curable material therein.

In still yet another embodiment, a method of implanting an elongate medical device through a burr hole is provided. The method includes securing a cranial anchor relative to the burr hole, wherein the anchor includes a base configured to secure to tissue surrounding the burr hole. The base may include an upper side, lower side, outer edge, and inner edge, wherein the inner edge defines an opening passing between the upper and lower sides. The anchor may also include a cup-shaped retention member comprising a sidewall and a floor forming a partially enclosed receptacle having an open top, wherein the receptacle may be configured to receive and retain a volume of curable material therein. The retention member may be removably received within the opening and secured to the base during implantation of the medical device, wherein the floor comprises a membrane operable to be pierced by the medical device, or by a tool used during implantation of the medical device. The method may further include: aligning a guide cannula with a predetermined device trajectory through the burr hole; inserting the guide cannula through the burr hole; puncturing the membrane with the guide cannula; inserting the medical device through the guide cannula; withdrawing the guide cannula from the burr hole; dispensing a volume of curable material into the retention member, wherein the volume of curable material is contained by the sidewall and floor; and curing the volume of curable material to immobilize a portion of the medical device relative to the retention member.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 2-3 illustrate diagrammatic views of a trajectory of an implanted medical device in two orthogonal planes, wherein: FIG. 2 illustrates the device trajectory when viewed normal to a first (e.g., sagittal) plane; and FIG. 3 when viewed normal to a second, intersecting and orthogonal (e.g., coronal) plane;

FIGS. 9 and 10 are section views illustrating an exemplary implantation procedure for use with the anchor of FIG. 4, wherein: FIG. 9 shows penetration of the retention member by a guide cannula; and FIG. 10 illustrates the medical device in place and after a curable material, e.g., cement, is dispensed into the retention member;

Figure 1:
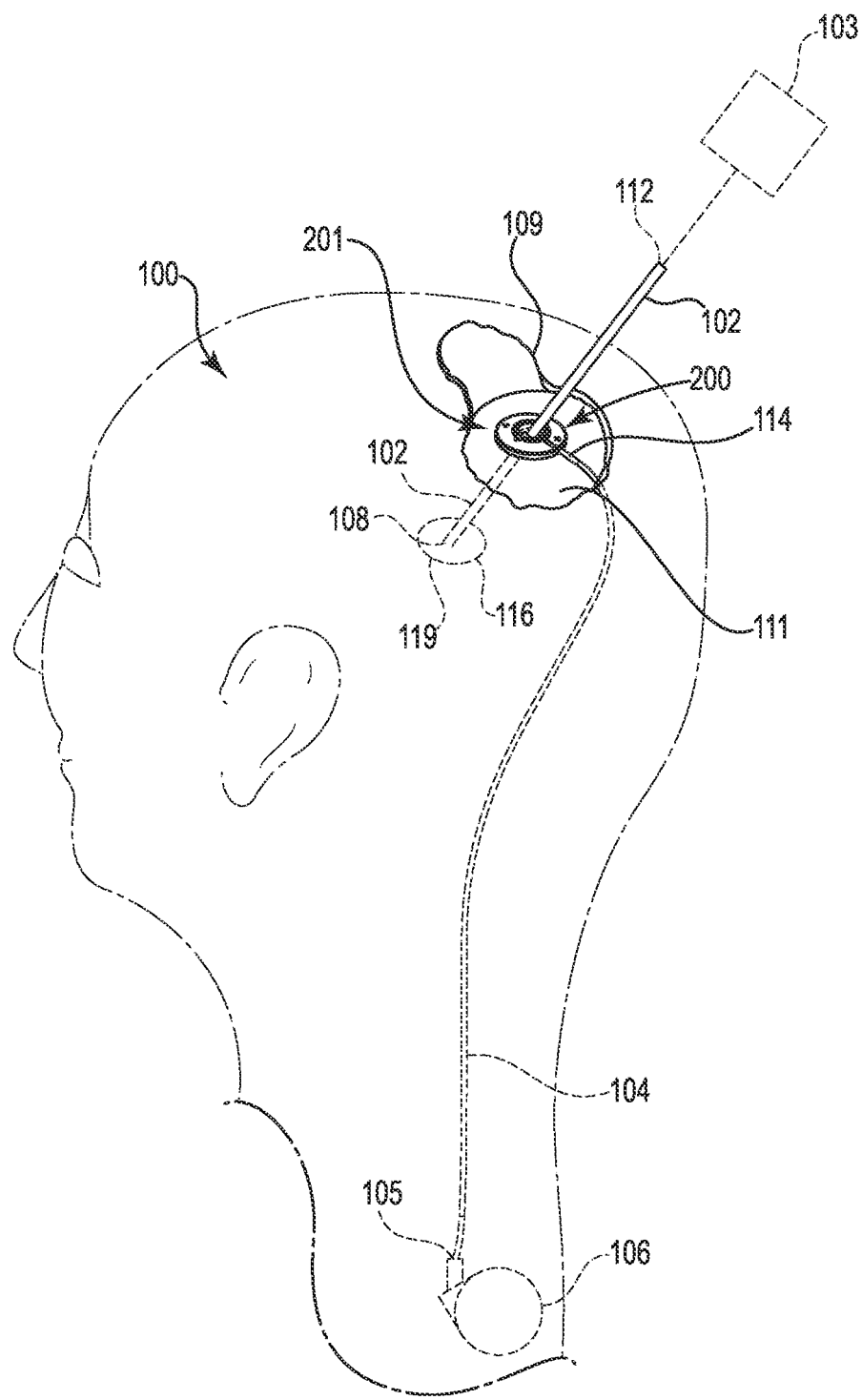
FIG. 1 illustrates an exemplary implantable infusion system, the system including an anchor system with a portal anchor, e.g., burr hole anchor, in accordance with one embodiment of the invention.

The figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments of the invention. The lack of illustration/description of such structure/components in a particular figure is, however, not to be interpreted as limiting the scope of the invention in any way.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Embodiments of the instant invention may be directed to body portal anchor devices and assemblies and to corresponding systems and methods for securing and strain relieving a medical device such as a therapy catheter or stimulation lead relative to a body portal. For example, exemplary anchors described herein may be configured to secure a therapy device such as an IPA therapy catheter routed through a cranial burr hole. While embodiments described herein may find use in acute treatment, they are particularly advantageous for long-term or chronic implantation, e.g., lasting several weeks or longer. Accordingly, devices in accordance with embodiments of the instant invention may provide a low profile, allowing them to be located sub-dermally, potentially for an indefinite period of time.

Systems in accordance with embodiments of the present invention may permit substantial isolation of at least a portion of the medical device (e.g., therapy catheter or lead) that is located inside the body portal from forces acting on a portion of the medical device that is outside the portal, e.g., forces resulting from bending or routing of the medical device outside the portal. Moreover, systems, anchors, and methods in accordance with embodiments of the present invention may accommodate implantation trajectories along most any axis through the burr hole. That is, anchors like those described herein may receive and secure the medical device along most any trajectory (e.g., normal to the skull or otherwise) and may further secure the device along such a trajectory without imparting excessive biasing forces that may shift the device from its implanted location or apply lateral pressure against tissue (e.g., against the cortex).

While exemplified herein in the context of burr hole anchors and corresponding infusion/electrical stimulation systems, anchors and systems in accordance with embodiments of the present invention may be advantageous for other applications. In fact, while described herein with reference to the treatment of neurological disorders, embodiments of the present invention may find use in most any system (e.g., medical or otherwise) that would benefit from portal anchoring of an elongate member.

It is noted that the terms "comprises" and variations thereof do not have a limiting meaning where these terms appear in the accompanying description and claims. Further, "a," "an," "the," "at least one," and "one or more" are used interchangeably herein. Moreover, relative terms such as "left," "right," "front," "forward," "aft," "rear," "rearward," "top," "bottom," "side," "upper," "lower," "above," "below," "horizontal," "vertical," and the like may be used herein and, if so, are from the perspective observed in the particular figure (or as observed when the apparatus is in a typical use orientation). These terms are used only to simplify the description, however, and not to limit the scope of the invention in any way.

With reference to the drawings, wherein like reference numerals designate like parts and assemblies throughout the several views, FIG. 1 diagrammatically illustrates an exemplary implantable therapy delivery system such as a brain infusion system 100 as it may be configured during use, e.g., implantation. Exemplary embodiments of the components described and illustrated herein may be sized for use with burr holes typical in human and other mammalian (e.g., primate) applications. For example, in one embodiment, a diameter of the burr hole 110 (see, e.g., FIG. 2) may be anywhere from about 6 millimeters (mm) to about 14 mm in diameter. However, such a configuration is not limiting as exemplary anchors could be scaled to accommodate most any size portal without departing from the scope of the invention.

The exemplary infusion system 100 may include a therapy source 106, and an anchor system 201. The anchor system 201 may include a cranial burr hole anchor device or assembly (referred to herein as "cranial anchor" or "anchor 200") and, in some embodiments, an elongate first medical tube, e.g., an intra-cranial IPA therapy catheter 102. The therapy catheter 102 may be partially implanted (e.g., such that it extends through the burr hole) within a brain 116 of a living being (e.g., human) such that a distal, therapy delivery tip or end 108 is located at a target tissue location 119 in the brain.

To assist with placement of the therapy catheter 102, a stereotactic apparatus (diagrammatically illustrated by reference number 103) as is known in the art may be utilized (see, for example, U.S. Pat. Pub. No. 2012/0083742 to Nelson). In the illustrated example, the therapy catheter 102 is implanted through a body portal, e.g., through a burr hole 110 (the burr hole is located underneath a burr hole anchor 200 in FIG. 1; but see FIGS. 2 and 8). The burr hole 110 may be formed in tissue (e.g., the bone forming the skull 111, which is represented underneath the scalp 109, the scalp being shown peeled back to provide access to the skull in FIG. 1).

Once the catheter 102 is accurately implanted through the burr hole in the skull (i.e., once the therapy delivery tip 108 is positioned at the predetermined target tissue location 119 in the brain 116), a proximal portion of the catheter 102 (the portion extending outside the burr hole) may be anchored with an anchor (anchor 200) in accordance with embodiments of the present invention.

A first end 112 of the therapy catheter 102 may extend outwardly through the anchor 200. In the illustrated embodiment, the first end 112 of the therapy catheter 102 (after disconnecting from the stereotactic apparatus and trimming to an appropriate length) may be operatively connected to a corresponding first end 114 of a feed or delivery catheter 104 (e.g., via a connector associated with the anchor, exemplary embodiments of which are described in U.S. Pat. Pub. No. 2011/0270187 to Nelson) of the system 100/system 201.

The delivery catheter 104 may have a second end 105 coupled to a therapy source or reservoir (e.g., an implantable infusion pump 106 such as a SynchroMed® II programmable infusion pump distributed by Medtronic, Inc., of Minneapolis, Minn. USA) containing a volume of the therapeutic agent. While described and illustrated herein utilizing an implantable infusion pump, this configuration is not limiting. For example, other embodiments may replace the pump with most any internal or external medicament delivery device, e.g., syringe, drip bag, etc.

The infusion system 100 may, in one embodiment, be configured to deliver a therapeutic agent for the treatment of a chronic ailment, e.g., convection-enhanced delivery (CED) of a therapeutic agent for the treatment of Huntington's disease. The therapeutic agent is delivered, via the catheters 102 and 104, from the pump 106 to the target tissue location 119 of the brain 116. This application is not limiting, however, as the system may be configured to deliver other therapeutic agents (e.g., such as for the treatment of Parkinson's or Alzheimer's disease) to the brain or to most any other region of the body.

As used herein, "therapeutic agents" may be a generic term referring to a fluid containing pharmaceutical compositions, genetic materials, biologics, and other substances. Pharmaceutical compositions may include, for example, antispasmodics, pain medications, chemotherapeutic agents, and the like. Genetic materials include substances intended to have a direct or indirect genetic therapeutic effect such as genetic vectors, genetic regulator elements, genetic structural elements, DNA, and the like. Biologics include substances that are living matter or derived from living matter intended to have a therapeutic effect such as stem cells, platelets, hormones, biologically produced chemicals, and the like. Other substances may include those that do not have a direct therapeutic effect such as, saline solutions, fluoroscopy agents, disease diagnostic agents, and the like. Accordingly, unless otherwise noted, the terms "therapeutic agent," "therapeutic substance," "drug," or "fluid" may be used interchangeably herein and may include most any therapeutic, diagnostic, or other substance that is delivered using the implantable systems and methods described herein.

Once again, while described above in the context of catheter implantation, the system 100, including the anchor 200, could also be configured to secure or anchor an elongate electrical element such as a stimulation lead via the burr hole. That is, the system could be an electrical stimulation lead system 100 in which a lead 102 is implanted such that its distal end 108 is positioned at the desired target tissue location 119. A proximal end 112 of the lead 102 could then, after disconnection from the stereotactic apparatus 103, be tunneled beneath the scalp 109 and connected to an electrical stimulation source 106 (in this embodiment, the lead 102 could connect to the stimulation source 106 via an intermediate extension 104).

With this general overview, the following description addresses various embodiments and aspects of exemplary anchors systems, as well as methods for using the same. While these embodiments may be described with some degree of particularity, they are nonetheless exemplary. That is, those of skill in the art will recognize that other embodiments are certainly possible without departing from the scope of the invention. Moreover, unless clearly stated otherwise, the medical devices described and illustrated in conjunction with any particular embodiment described may be either a therapy catheter or an electrical lead. As a result, the terms "medical device" (or "device"), "therapy catheter" (or "catheter"), and "electrical lead" (or "lead") may be used herein to refer to most any elongate member.

Figure 2:
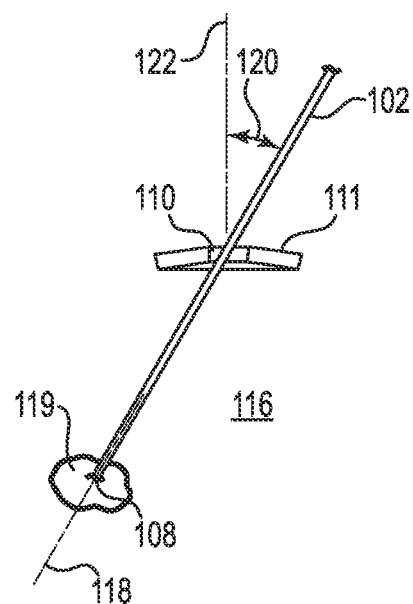
Figure 3:
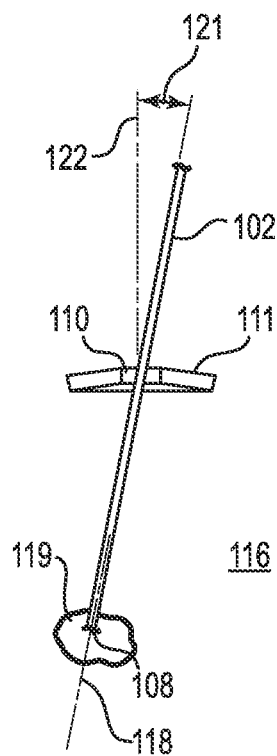

FIGS. 2 and 3 are exemplary diagrammatic illustrations of the medical device 102 implanted through the burr hole 110 formed in the skull 111 (anchor 200 removed for clarity in these views), with FIG. 2 showing a view looking normal to a first (e.g., sagittal) plane and FIG. 3 showing a view looking normal to a second intersecting, orthogonal (e.g., coronal) plane. As clearly indicated in these views, the stereotactically-guided trajectory 118 (which may also be referred to herein as an "axis" 118) of the device 102 may be selected to intersect the target tissue location 119 within the brain 116. As further illustrated in these views, the trajectory 118 may be along an axis that is slanted relative to a line 122 normal to the tissue (e.g., slanted relative to a line normal to the skull bone) surrounding the burr hole. That is, the trajectory 118 may be oriented such that it is neither coaxial nor parallel to an axis (the axis being coincident and co-identified with line 122) of the burr hole 110.

For instance, when viewed normal to the first (e.g., sagittal) plane as shown in FIG. 2, the trajectory axis 118 is slanted at an angle 120 from the axis 122. Moreover, the trajectory 118 may also be slanted, relative to the axis 122, when viewed normal to the second (e.g., coronal) plane at an angle 121. That is to say, the trajectory 118 may be skewed from normal relative to one or both of these mutually perpendicular planes. Anchors in accordance with embodiments of the present invention are configured to secure the medical device, without undesirably imparting anchor forces that could ultimately bias the therapy delivery tip 108 away from the target tissue location 119. This advantage may be realized regardless of whether the device trajectory 118 is parallel to the axis 122, or is instead slanted (in one or both planes) relative to the axis such as illustrated in FIGS. 2 and 3. While not wishing to be bound to any particular orientation, the angles 120 and 121 could be about 30 degrees or less, e.g., 25 degrees or less.

Figure 4:
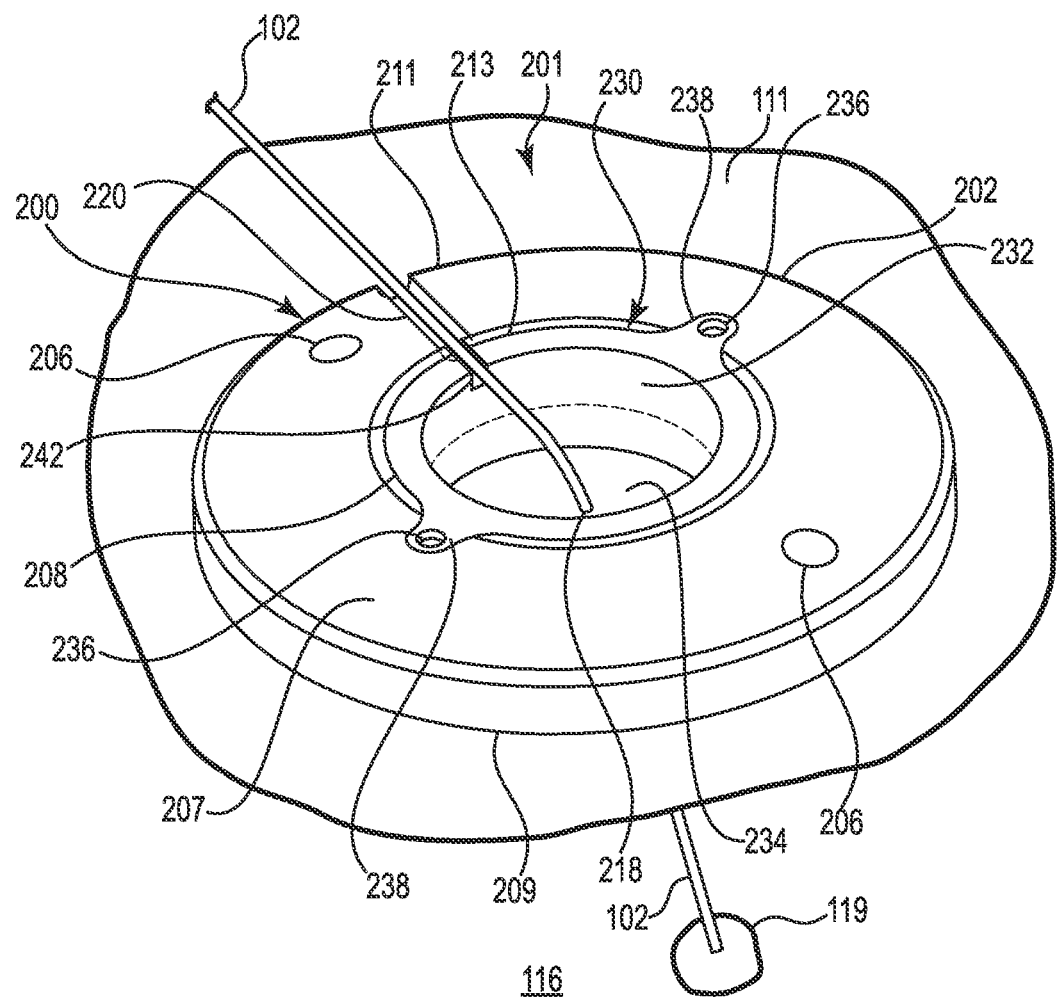
FIG. 4 is an upper perspective view of an anchor system including an anchor in accordance with one embodiment of the invention.

FIGS. 4-8 illustrate various views of the anchor system 201 including the burr hole anchor 200 in accordance with one exemplary embodiment of the invention. With reference to FIG. 4, the anchor 200 may include an annular base 202 that may be positioned to surround the burr hole 110 (covered by the anchor in FIG. 4, but see FIG. 8). The anchor 200 (e.g., the base 202) is operable to secure to the tissue, e.g., to an outer surface of the bone (skull 111), surrounding the burr hole 110 via any acceptable method. In the illustrated embodiment, the base 202 is secured with bone screws (not shown) extending through openings (e.g., holes 206) formed through the base 202 and threaded into the skull 111.

The base 202 may include an upper side 207, a lower side 209, a peripheral or outer edge 211, and an inner edge 213. The inner edge 213 may define an opening 208 (see FIG. 6) passing through the base 202 between the upper and lower sides 207 and 209. The upper side 207 may optionally define a groove 220 extending from the inner edge 213 to and through the outer edge 211 as shown in FIG. 4. The groove 220, which may form an open-faced trough, may be sized to accommodate the medical device 102 once the device is bent (e.g., at about 90 degrees) and placed therein. While not illustrated, the groove 220 may accommodate a connector for connection of the medical device 102 (e.g., therapy catheter) with the delivery catheter 104 (see FIG. 1). For example, see U.S. Patent Application Publication No. 2011/0270187.

Figure 8:
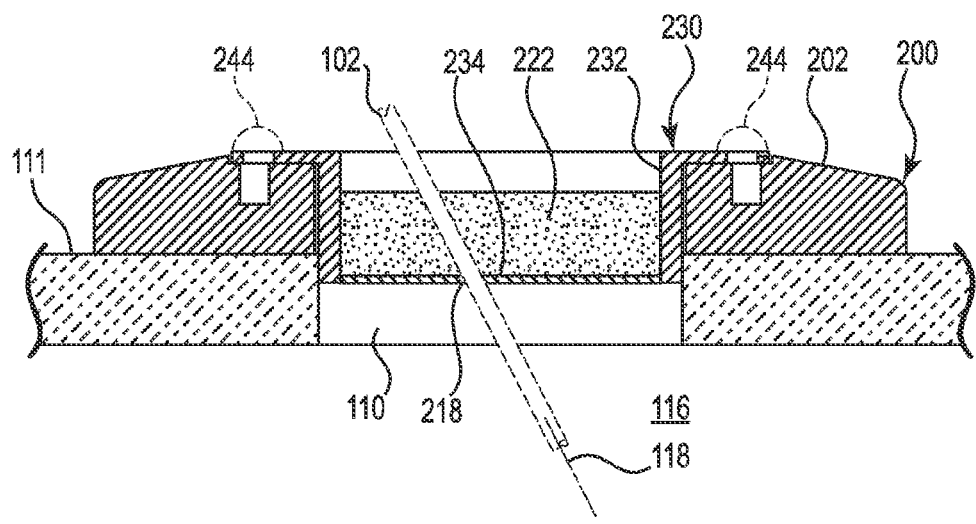
FIG. 8 is a section view taken along line 8-8 of FIG. 7.

The anchor 200 may also include a retention member 230. In one embodiment, the retention member may be cup-shaped as perhaps best illustrated in FIG. 6. The retention member 230 may be configured to be received within the opening 208 and secure to the base during implantation of the medical device 102. As shown in the figures, the retention member may include a sidewall 232 and a floor 234, the floor positioned at an elevation at or near (e.g., slightly below) the lower side of the base when the retention member is secured to the base within the opening as shown in FIG. 8. The floor 234 may form a barrier proximate tissue of the brain 116 (e.g., between the brain and the surgeon) during the surgical procedure. As further described below, the medical device 102 may extend through the floor 234 at any one of two or more locations, e.g., at an aperture 218. The floor 234 is preferably at an elevation that provides sufficient room above the floor to bend the medical device 90 degrees as shown in FIG. 4 without kinking, occluding, or otherwise damaging the medical device.

In one embodiment, the retention member 230 may be removably attached (secured) to the base 202, e.g., using fasteners 244 (see FIG. 8) passing through openings 236 formed on ears 238 of the retention member 230 and threadably engaged with the upper side 207 of the base as indicated in FIGS. 4 and 8. However, other embodiments may secure the retention member 230 to the base 202 in most any fashion without departing from the scope of the invention. As shown in the figures, the retention member 230 (as well as the retention member 330 described below), may define a cup-shaped receptacle (e.g., a partially enclosed, open top receptacle) configured to receive and retain a volume of curable material therein as will be further described below. Accordingly, a curable material as described below may be dispensed into the receptacle in a flowable form, wherein the curable material, once cured, is configured to bond to the retention member and to the medical device to immobilize the medical device relative to the retention member.

Figure 5:
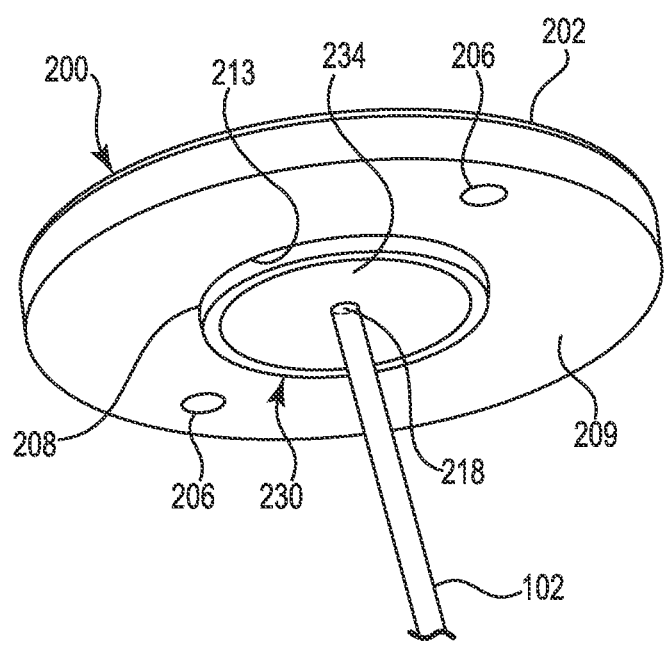
FIG. 5 is a lower perspective view of the anchor of FIG. 4.

FIG. 5 illustrates a bottom perspective view of the anchor 200 with the retention member 230 secured in the opening 208 and the medical device 102 shown passing through the aperture 218.

Figure 6:
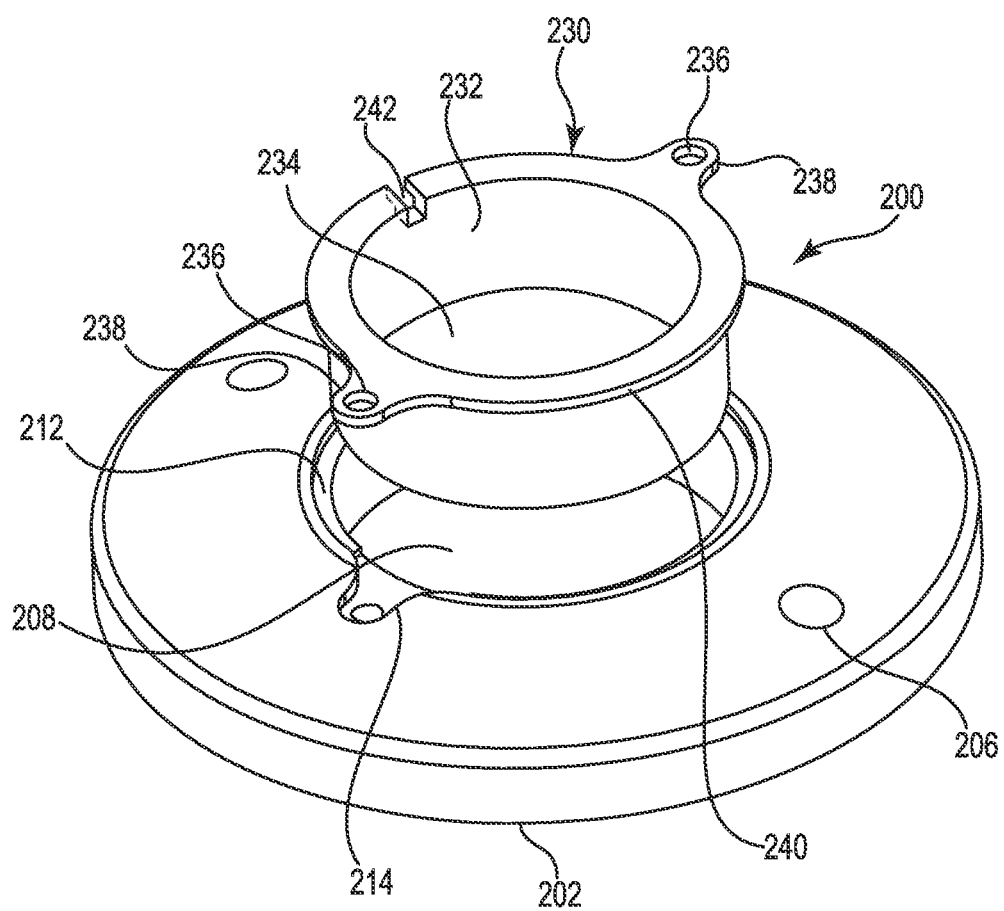
FIG. 6 is an exploded view of the anchor of FIG. 4 showing a base and a retention member in accordance with one embodiment of the invention.

FIG. 6 illustrates the anchor 200 with the retention member 230 exploded therefrom. As shown in this view, the retention member 230 may include a flange 240 extending outwardly from an upper edge of the sidewall 232. The flange may be configured to seat against a ledge 212 of the base 202 when the retention member 230 is fully received within the opening 208. The base 202 may further include cutouts 214 in the upper surface configured to accommodate the ears 238 of the retention member 230.

In embodiments that utilize the groove 220 (see FIG. 4) formed in the upper side 207 of the base, the retention member 230 may also include a cutout 242, e.g., formed in the sidewall 232 and flange 240, to accommodate the medical device as shown, for example, in FIG. 4. In other embodiments, the groove 220 and cutout 242 may be optional (see, e.g., FIG. 7).

Figure 7:
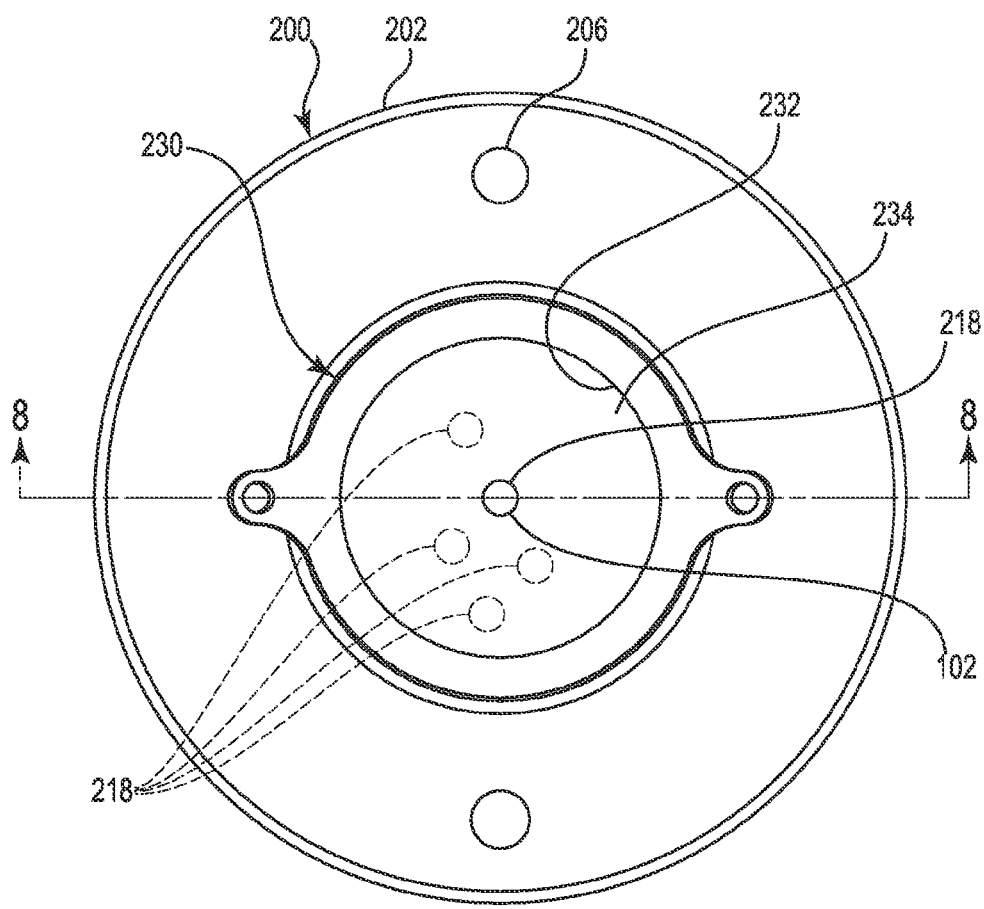
FIG. 7 is a top plan view of the anchor of FIG. 4.

FIG. 7 illustrates a top plan view of the anchor 200 with the medical device 102 partially shown passing through the floor 234 at the aperture 218. As shown in this view, the aperture 218 may be positioned at most any point on the floor 234. That is, the location and trajectory at which the medical device 102 penetrates the floor may be selected by the surgeon to best achieve the desired implant trajectory 118 (see FIG. 8) through the burr hole 110. Moreover, while shown in FIG. 7 as penetrating the floor 234 in a generally perpendicular orientation, the aperture 218 may permit most any medical device trajectory 118 as shown in FIG. 8.

To accommodate these various locations, the sidewall 232 of the retention member 230 may include a first material while the floor includes a second material different than the first material. For example, the floor 234 may, in one embodiment, be a membrane formed of a material selected from the group consisting of silicone, fabric, cellular foam, and absorbable gelatin. In one embodiment, the membrane may be made from GORE-TEX® fabric distributed by W. L. Gore and Associates, Inc. of Newark, Del. USA, and over-molded with, or glued to, the sidewall 232. Such materials may provide a floor 234 that may be pierced or penetrated by the medical device 102, or by an associated implantation tool, without excessive tearing beyond the penetration location. As a result, the floor 234 may remain sufficiently able to contain a biocompatible, curable material 222 as shown in FIG. 8 (and further described below) after penetration by the medical device 102. The remainder of the retention device 230 (e.g., the sidewall 232), as well as the base, 202, may, in one embodiment, be made from a hard plastic (e.g., polysulfone or polyetheretherketone (PEEK)) or metal such as grade 2 or grade 5 Titanium.

In an exemplary implant procedure, an incision may be made in the patient's scalp 109 (see FIG. 1), after which the scalp may be pulled back to expose the skull 111 (see FIG. 8). After forming the burr hole 110, the base 202 may be secured to the skull 111 using fasteners (not shown) passing through the openings 206 and threaded into the skull. At this point, the retention member 230 may be placed within the central opening 208 and attached in place, e.g., using fasteners 244 (see FIG. 8).

Figure 9:
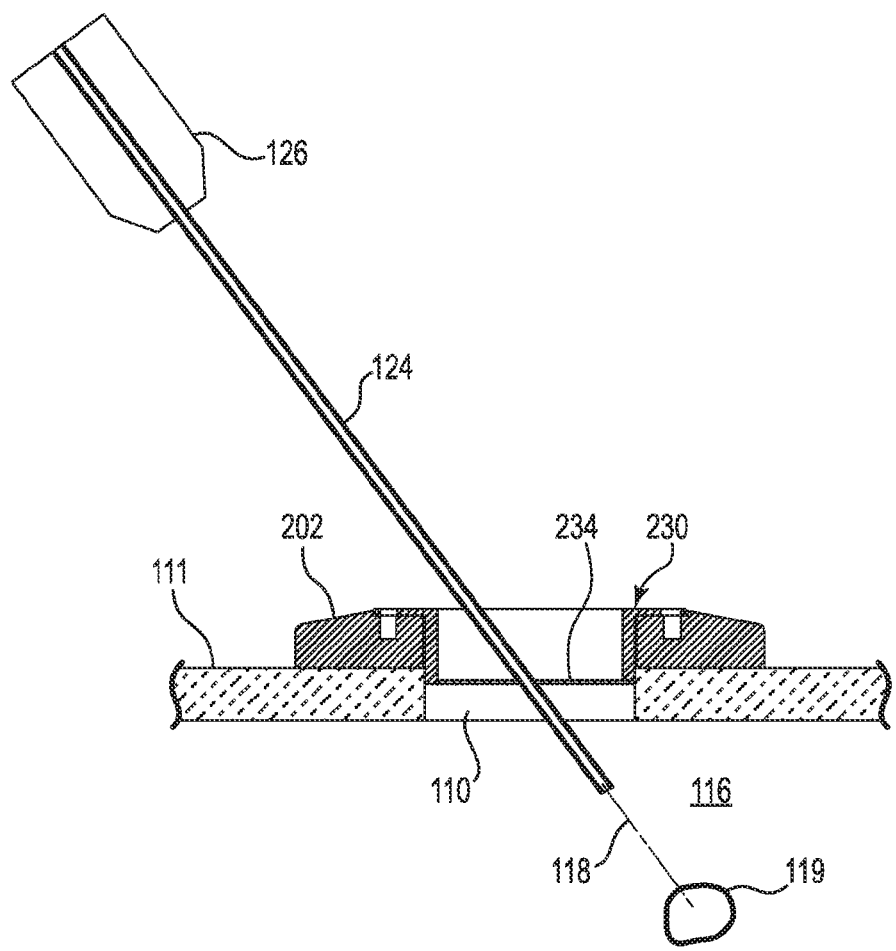

A guide cannula 124 may be attached to a headframe guide adapter 126 of the stereotactic apparatus 103 (see FIG. 1) as shown in FIG. 9. The sterectotactic apparatus 103 may then be configured such that an axis of the guide cannula 124 aligns with the target tissue location 119 within the brain 116. That is, the guide cannula 124 may be configured such that its axis (i.e., the intended medical device trajectory 118) intersects with the target tissue location 119 as shown in FIG. 9. The guide cannula 124 may then be advanced until the distal end of the guide cannula penetrates the floor 234 of the retention member 230 as also shown in FIG. 9.

The guide cannula 124 may then be advanced, in accordance with accepted techniques, until its distal end is at or near the target tissue location 119. The medical device 102 (lead or catheter) may then be inserted into the guide cannula 124 in accordance with known techniques until the therapy delivery tip 108 of the device 102 is at the target tissue location 119 as shown in FIG. 10.

Figure 10:
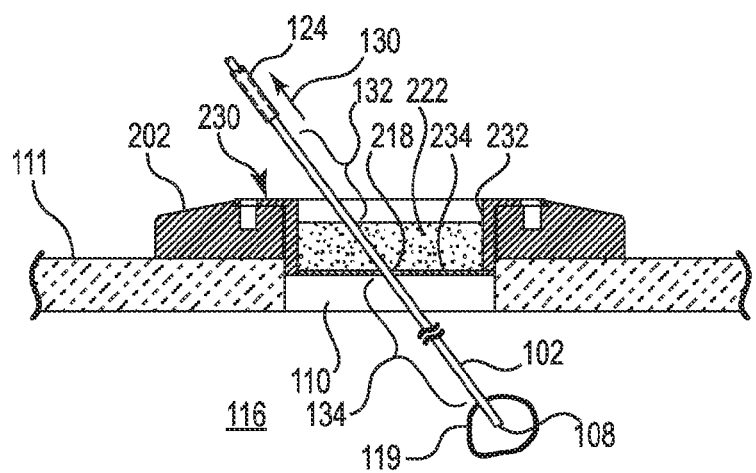

When the medical device 102 has been positioned, the guide cannula 124 may be retracted (moved in the direction 130 as shown in FIG. 10) while holding the device 102 in place, e.g., with a stylet (not shown) and the stereotactic apparatus 103. After stylet removal and bending of the medical device 102 (e.g., into the groove 220 as shown in FIG. 4), or while still holding the medical device in place with the stylet, curable material such as bone cement 222, in a flowable or viscous form, may be dispensed into the receptacle of the retention member 230. While illustrated as cement 222, other materials (e.g., epoxy, bone graft, silicone rubber, or the like) are also contemplated within the scope of the invention. Once cured, the cement 222 may bond to the retention member (e.g., the sidewall 232 and floor 234) and to the medical device 102 to immobilize the medical device relative to the retention member, and thus relative to the base 202.

The sidewall 232 and floor 234 may assist with containing the cement during curing. Even though the floor was penetrated by the larger guide cannula 124, the aperture formed by such penetration is relatively small so as to not permit appreciable volume of the cement 222 to flow through the floor and into the brain after cannula retraction. In addition to containing the cement 222, the floor 234 (and floor 334 described below) may further insulate the brain and dura from any heat that may result from exothermic activity during curing of the cement. Thus, the floor 234 acts as a barrier to assist with containing the cement during curing.

After curing, the stylet may be withdrawn (if not already) and the medical device 102 may be connected, via its exposed end 112, to a therapeutic source (e.g., pump or electrical stimulation source 106 as shown in FIG. 1). Once again an intermediate member (see, e.g., delivery catheter 104) may be used between the medical device 102 and the therapeutic source 106.

The cement 222 may isolate a second portion 134 of the medical device (e.g., that part located below the floor) from a first portion 132 (see, e.g., FIG. 10) of the medical device 102 (e.g., that part located above the cement 222 in FIG. 10). As a result, forces acting on the first portion 132, e.g., forces resulting from bending the catheter (see FIG. 4), may have little, if any, effect on the second portion 134. That is, due to the isolation/relief properties of the cement 222, the medical device 102 may be bent or routed in most any direction without concern for imparting biasing forces that could displace the therapy delivery tip 108.

In an alternative embodiment, the retention member 230 could slide over the exposed distal end of the guide cannula 124 before the cannula is lowered through the base 202 and into the burr hole. With the retention member 230 held near the guide adapter 126, the guide cannula may be advanced toward the target tissue location 119 as shown in FIG. 9. Once the guide cannula is at least near the dura and the trajectory 118 is established, the retention member 230 may be slid down the cannula until it seats within the opening 208 of the base 202 as described herein, after which it may be secured, e.g., using the fasteners 244 shown in FIG. 8. Such an alternative procedure may be beneficial in some circumstances. For example, where the floor 234 is constructed of a stretchy material such as silicone, the surgeon may need to manually support a lower side of the floor to permit the guide cannula to penetrate the floor without causing excessive stretching or damage to the floor.

By making the retention member 230 removable from the base 202, the anchor 200 may also be beneficial in the instance where the medical device requires subsequent removal (e.g., where subsequent imaging indicates that the therapy delivery tip was mislocated). For instance, the medical device 102 may be removed by simply removing the entire retention member 230 (e.g., removing the fasteners 244 and extracting the retention member and medical device as a single unit), or by breaking up the cement 222 within the retention member. In case of the latter, the retention member 230 may contain the cement 222 therein during cement extraction, reducing the opportunity for cement to fall into the burr hole.

Figure 11:
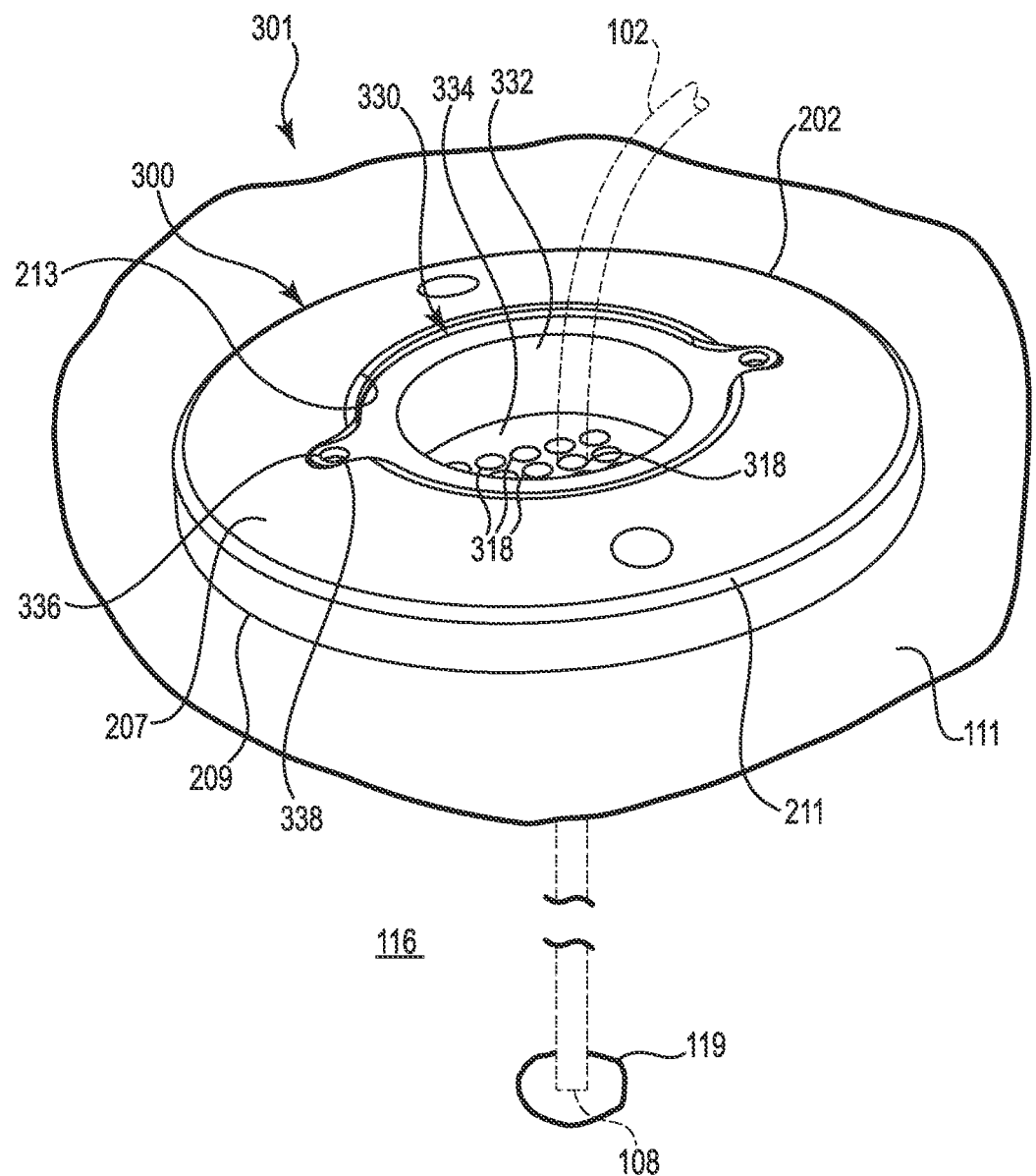
FIG. 11 is an upper perspective view of an anchor system including an anchor in accordance with another embodiment of the invention.

FIGS. 11-15 illustrate various views of an anchor system 301 including a burr hole anchor 300 in accordance with another exemplary embodiment of the invention. With reference to FIG. 11, the anchor 300 may include the annular base 202 (as already described herein), wherein the base 202 is positionable to surround the burr hole 110 (covered by the anchor in FIG. 11, but see FIG. 15). The anchor 300 (e.g., base 202) is, once again, operable to secure to the tissue, e.g., to an outer surface of the bone (skull 111), surrounding the burr hole 110 via any acceptable method.

The base 202, as described above, may include the upper side 207, lower side 209, peripheral or outer edge 211, and inner edge 213, with the inner edge 213 defining the opening 208 (see FIG. 13) passing through the base 202 between the upper and lower sides 207 and 209. Although not shown FIGS. 11-15, the upper side 207 may optionally define the groove 220 extending from the inner edge 213 to and through the outer edge 211 as shown in FIG. 4.

Figure 13:
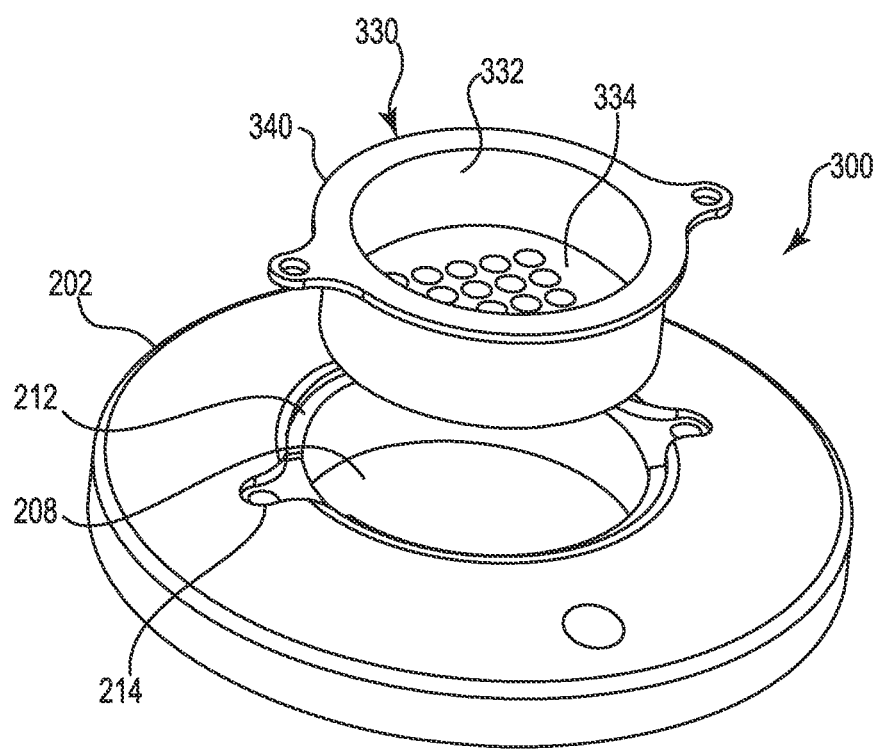
FIG. 13 is an exploded view of the anchor of FIG. 11 showing a base and a retention member in accordance with one embodiment of the invention.
Figure 15:
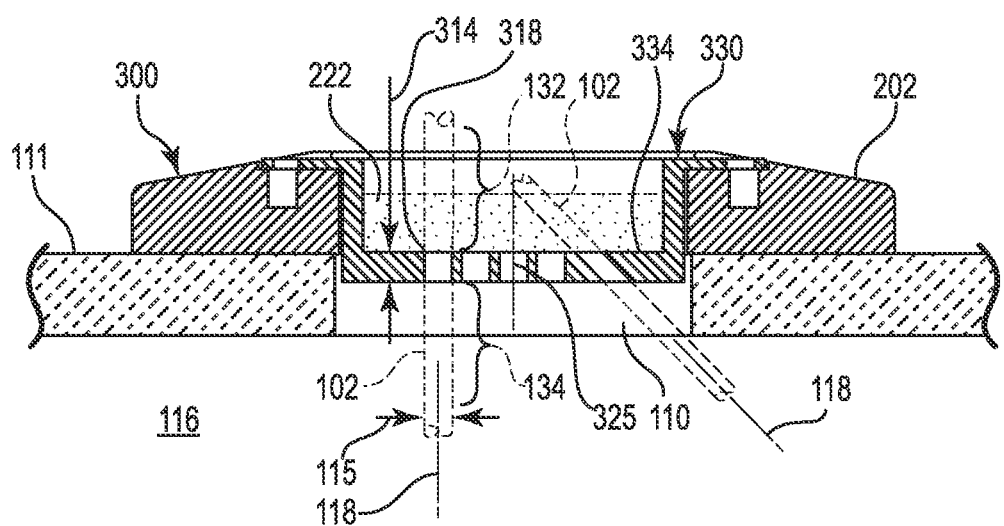
FIG. 15 is a section view taken along line 15-15 of FIG. 14.

Unlike the anchor 200, the anchor 300 may include a retention member 330 in accordance with another embodiment of the invention. However, in one embodiment, the retention member 330 may still be cup-shaped as best illustrated in FIG. 13, and is further configured to be received within the opening 208 and secure to the base 202 before or during implantation of the medical device 102. As shown in the figures, the retention member 330 may, like the member 230, include a sidewall 332 connected to a floor 334 to form an open top receptacle configured to optionally receive therein the volume of curable material (e.g., cement 222). The floor 334 may be positioned at an elevation at or near the lower side of the base when the retention member is secured to the base within the opening as shown in FIG. 15. The floor 334 may form a barrier proximate tissue of the brain 116 (e.g., between the dura and the environment) during the surgical procedure. As further described below, the medical device 102 may extend through the floor 334 at any one of two or more locations, e.g., apertures 318.

In one embodiment, the retention member 330 may, like the member 230, be removably received within the opening 208 and secured to the base 202, e.g., using fasteners 244 (see FIG. 8) passing through openings 336 formed on ears 338 of the retention member 330 and threadably engaged with the upper side 207 of the base as already described with reference to the anchor 200 in FIG. 8. However, other embodiments may secure the retention member 330 to the base 202 in most any fashion without departing from the scope of the invention.

Figure 12:
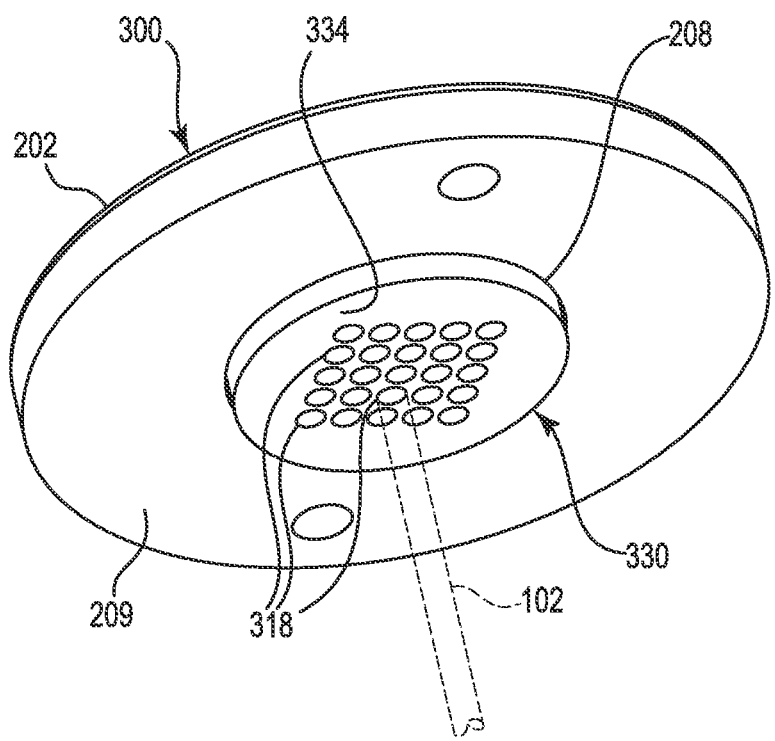
FIG. 12 is a lower perspective view of the anchor of FIG. 11.

FIG. 12 illustrates a bottom perspective view of the anchor 300 with the retention member 330 secured in the opening 208 of the base 202. As shown in this view, the medical device 102 may pass through any one of two or more apertures 318 formed in the floor 334 of the retention member 330.

FIG. 13 illustrates the anchor 300 with the retention member 330 shown exploded from the base 202. As shown in this view, the retention member 330 may include a flange 340 extending outwardly from an upper edge of the sidewall 332, the flange configured to seat against the ledge 212 (using cutouts 214) of the base when the retention member is fully received within the opening 208 as already described herein. Although not illustrated, the retention member 330 could also include a cutout to accommodate the medical device 102 (e.g., similar to the cutout 242 shown in FIGS. 4 and 6).

Figure 14:
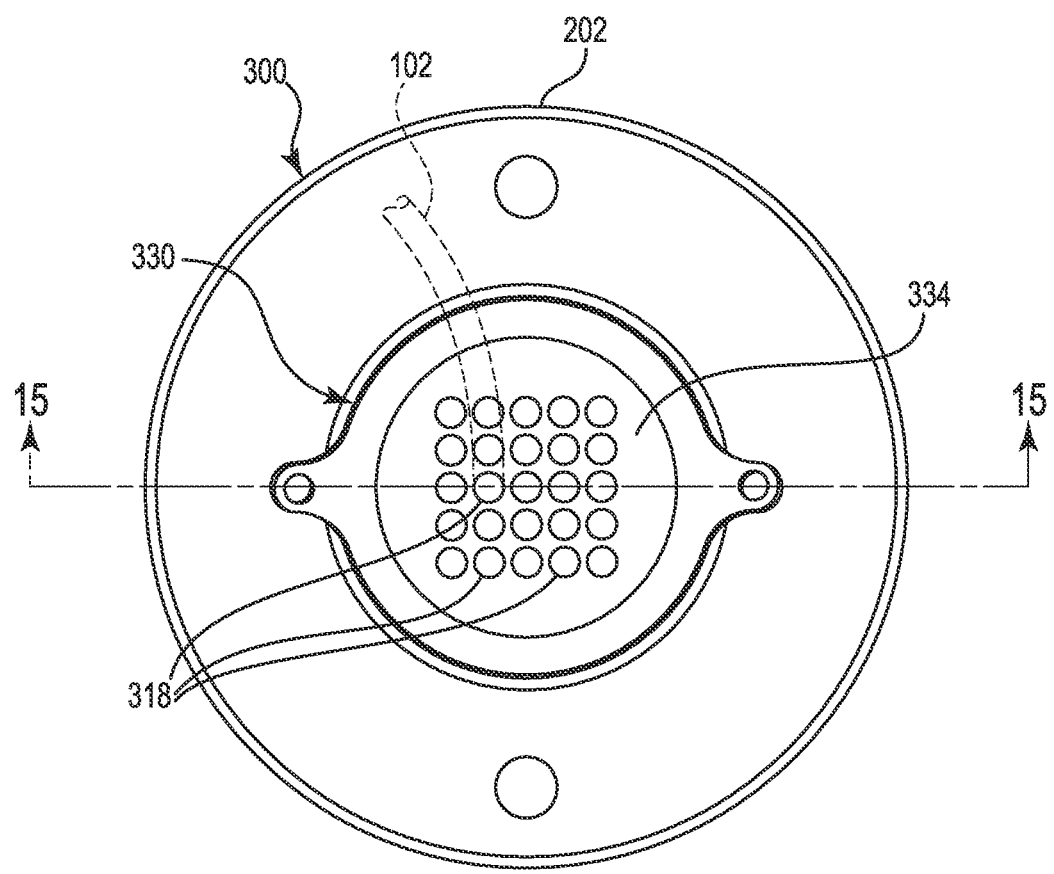
FIG. 14 is a top plan view of the anchor of FIG. 11.

FIG. 14 illustrates a top plan view of the anchor 300 with the medical device 102 shown extending through the floor 334 at an aperture 318. Unlike the floor 234, the floor 334 may include a plurality of apertures 318, wherein each of the apertures is configured to receive therein the medical device with clearance.

As shown in FIGS. 11-15, the apertures 318 may be positioned at most any point on the floor 234. In the illustrated embodiment, the apertures may form an array, e.g., a five-by-five array, to accommodate medical device insertion at most any lateral location through the burr hole 110. As illustrated in FIGS. 14-15, one or more of the apertures 318 may include a centerline axis 325 normal to an upper surface of the floor 334. However, as shown in FIG. 15, such a construction is exemplary only as, in other embodiments, a centerline axis of one or more of the apertures 318 could be angled (see alternative depiction of device 102 in FIG. 15) relative to an upper surface of the floor. While the floor 234 is formed by a penetrable membrane, the floor 334 (as well as the sidewall 332 and flange 340) may be relatively rigid, e.g., made from plastic (e.g., polysulfone or PEEK) or metal such as grade 2 or grade 5 Titanium.

Each aperture 318 may be configured to receive the medical device 102 with a slight clearance fit. For example, the diameter of the apertures 318 may be about 2 mm to accommodate a medical device 102 having an outer diameter 115 of about 1.8 mm (see FIG. 15). In the illustrated embodiment, each aperture 318 may further have a length 314 (corresponding to a thickness of the floor 334) that is about two or more times (e.g., 2-4 times) greater than the dimension of the outer diameter 115 (see FIG. 15) of the medical device 102. By providing a floor 334 of this thickness, movement of the first portion 132 of the medical device 102 (e.g., from bending) may be effectively isolated from the second portion 134 (see FIG. 15), even though the medical device is received with clearance through the aperture 318.

Optionally, the retention member 340 may, like the retention member 240, receive therein a volume of curable material (e.g., cement 222) after the medical device 102 is located. The viscosity of the cement 222 may be selected to reduce flow of uncured cement through the apertures 318 and into the brain.

In yet other embodiments, the retention member 330 may be removably received within the opening with some lateral or rotational leeway such that the retention member may be moved slightly side-to-side, or rotationally, to better allow alignment of the device trajectory 118 with one of the apertures 318. For example, the openings 336 (see FIG. 1) may be formed as linear or arcuate slots to accommodate some lateral movement of the retention member relative to the base. In addition or alternatively, the cutouts 214 (see FIG. 13) could extend around a portion of the inner surface 213 (and/or be located at multiple, angular positions around the opening 208) and provide a plurality of threaded openings to receive the fasteners 244 (see FIG. 8), thus allowing some rotational variation in the location of the retention member 340 relative to the base 202. Still further, a variety of retention members could be provided as a kit, wherein each retention member has apertures in different patterns and/or different trajectories to accommodate a multitude of implantation scenarios.

An exemplary surgical procedure using the anchor 300 may again include forming the burr hole 110, after which the base 202 may be placed over and attached to the skull 111. The procedure may differ somewhat, however, from the procedure described above with respect to the anchor 200 in the following ways.

Figure 16:
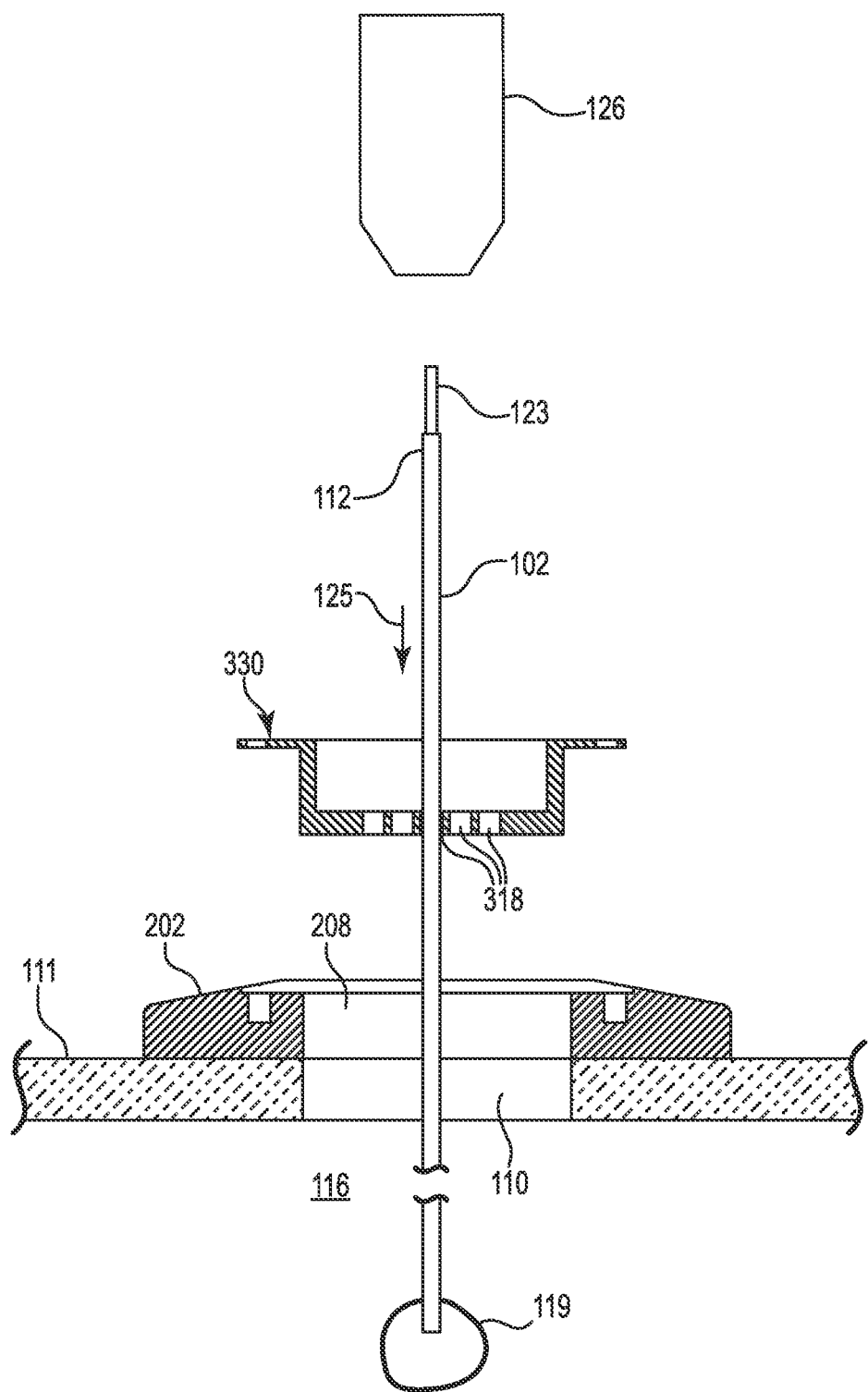
FIG. 16 illustrates an exemplary implantation procedure for use with the system of FIG. 11.

The guide cannula 124 may again be attached to the headframe guide adapter 126 of the stereotactic apparatus 103 (see FIG. 1) as already described herein (see, e.g., FIG. 9) and the guide cannula 124 advanced until the distal end of the guide cannula penetrates the burr hole 110 and advances until its distal end is at or near the target tissue location 119. The medical device 102 (lead or catheter) may then be inserted into the guide cannula 124 in accordance with known techniques (e.g., using a stylet 123 as shown in FIG. 16) until the therapy delivery tip 108 of the device 102 is at the target tissue location 119 (see, e.g., FIG. 10).

When the medical device 102 has been positioned, the guide cannula 124 may be retracted (moved in the direction 130 as shown in FIG. 10) while holding the device 102 in place, e.g., with the stylet 123 and the stereotactic apparatus 103 (see FIG. 1). After identifying the approximate location of the trajectory through the burr hole 110, the surgeon may disconnect the stylet 123 from the guide adapter 126 as shown in FIG. 16. With the end 112 of the medical device 102 now exposed, the surgeon may identify the most appropriate aperture 318 corresponding to the lateral location of the medical device within the burr hole 110. The retention member 330 may then be placed over the exposed end 112 of the medical device 102 and stylet 123 such that the medical device enters the appropriate aperture 318 of the retention member 330. The retention member 330 may then be slid down the medical device 102 (e.g., in the direction 125) as shown in FIG. 16. Once the retention member 330 seats within the opening 208 of the base, the retention member can be secured to the base (e.g., using the fasteners 244 shown in FIG. 8).

If used, the cement 222 may be added before (or after) withdrawing the stylet 123 from the medical device. Once again, even though the floor 334 includes multiple apertures 318, they are preferably too small to permit appreciable volume of cement 222 to flow through the floor and into the brain. Thus, once again, the floor 334 may act as a barrier to assist with containing the cement during curing.

After curing, the stylet may be withdrawn and the medical device 102 may be connected, via its exposed end, to a therapeutic source (e.g., pump or electrical stimulation source 106 as shown in FIG. 1). Once again, due to the isolation/relief properties of the floor 334 and/or cement 222, biasing forces (e.g., from bending or routing the portion of the medical device 102 outside the burr hole) that could displace the therapy delivery tip 108 of the medical device may be reduced or eliminated.

While described herein as accommodating a single medical device through the burr hole, those of skill in the art will realize that embodiments of the present invention may accommodate multiple medical devices implanted through a single burr hole, with each device oriented along its own trajectory, without departing from the scope of the invention.

Burr hole anchors and systems in accordance with embodiments of the present invention may provide various benefits including, for example, reducing or eliminating migration-inducing biasing forces applied to an implanted medical device resulting from bends formed in the medical device. Moreover, anchors in accordance with embodiments described herein may reduce or minimize such biasing forces while also accommodating most any device trajectory through the burr hole. This increased flexibility in device placement, along with less likelihood of tip migration, may provide advantages over other anchor designs.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are described and reference has been made to possible variations within the scope of this invention. These and other variations, combinations, and modifications of the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A cranial anchor configured to secure an elongate medical device implanted via a burr hole, the anchor comprising:
   a base configured to secure to tissue surrounding the burr hole, the base comprising an upper side, lower side, outer edge, and inner edge, the inner edge defining an opening passing between the upper and lower sides;
   a cup-shaped retention member comprising a sidewall and a floor, the retention member configured to be received within the opening and secured to the base, the floor positioned at an elevation at or near the lower side of the base when the retention member is secured to the base within the opening, wherein the floor is configured to permit passage of the medical device through the floor at any one of two or more locations, the sidewall and floor defining a receptacle configured to receive and retain a volume of curable material therein; and
   curable material configured to be dispensed into the receptacle in a flowable form, wherein the curable material, once cured, is configured to bond to the retention member and to the medical device to immobilize the medical device relative to the retention member.

2. The anchor of claim 1, wherein the floor comprises two or more apertures formed therethrough, each aperture configured to permit passage of the medical device.

3. The anchor of claim 2, wherein each aperture has a length that is two or more times greater than a dimension of an outer diameter of the medical device.

4. The anchor of claim 2, wherein each aperture includes a centerline axis normal to an upper surface of the floor.

5. The anchor of claim 1, wherein the floor comprises a membrane configured to be pierced by the medical device, or by a tool used during implantation of the medical device.

6. The anchor of claim 5, wherein the membrane comprises a material selected from the group consisting of silicone, fabric, cellular foam, and absorbable gelatin.

7. The anchor of claim 1, wherein the retention member is configured to be removably attached to the base.

8. A cranial anchor configured to secure an elongate medical device implanted via a burr hole, the anchor comprising:
   a base configured to secure to tissue surrounding the burr hole, the base comprising an upper side, lower side, outer edge, and inner edge, the inner edge defining an opening passing between the upper and lower sides;
   a cup-shaped retention member comprising a sidewall and a floor forming a partially enclosed receptacle having an open top, the receptacle configured to receive and retain a volume of curable material therein, the retention member configured to be removably received within the opening and secured to the base, wherein the floor comprises a membrane operable to be pierced by the medical device, or by a tool used during implantation of the medical device; and
   curable material configured to be dispensed into the receptacle in a flowable form, wherein the curable material, once cured, is configured to bond to the retention member and to the medical device to immobilize the medical device relative to the retention member.

9. The anchor of claim 8, wherein the floor is positioned at an elevation at or near the lower side of the base when the retention member is secured to the base within the opening.

10. The anchor of claim 8, wherein the membrane comprises a material selected from the group consisting of silicone, fabric, cellular foam, and absorbable gelatin.

11. The anchor of claim 8, wherein the sidewall comprises a first material and the floor comprises a second material different than the first material.

12. A cranial anchor configured to secure an elongate medical device implanted via a burr hole, the anchor comprising:
a base configured to secure to tissue surrounding the burr hole, the base comprising an upper side, lower side, outer edge, and inner edge, the inner edge defining an opening passing between the upper and lower sides;
a cup-shaped retention member configured to be removably received within the opening and secured to the base, the retention member defining a floor positioned at an elevation at or near the lower side of the base when the retention member is secured to the base within the opening, the floor defining a plurality of apertures, wherein each aperture is configured to receive therein the medical device with clearance, wherein the retention member further comprises a sidewall connected to the floor, wherein the floor and sidewall form an open top receptacle configured to receive therein a volume of curable material; and
curable material configured to be dispensed into the receptacle in a flowable form, wherein the curable material, once cured, is configured to bond to the retention member and to the medical device to immobilize the medical device relative to the retention member.

13. The anchor of claim 12, wherein each aperture has a length that is two or more times greater than a dimension of an outer diameter of the medical device.

14. The anchor of claim 12, wherein a centerline axis of one or more of the apertures is normal to a plane containing an upper surface of the floor.

15. An implantable therapy delivery system comprising:
an elongate medical device configured to extend through a burr hole of a living being, the medical device comprising a therapy delivery tip for placement at a target tissue location within the living being;
a therapy source configured to connect to the medical device; and
a cranial anchor configured to secure the medical device at or near the burr hole, the anchor comprising:
a base configured to secure to tissue surrounding the burr hole, the base comprising an upper side, lower side, outer edge, and inner edge, the inner edge defining an opening passing between the upper and lower sides;
a cup-shaped retention member comprising a sidewall and a floor, the retention member configured to be received within the opening and secured to the base, the floor positioned at an elevation at or near the lower side of the base when the retention member is secured to the base within the opening, wherein the floor is configured to permit passage of the medical device through the floor at any one of two or more locations, the sidewall and floor defining a receptacle configured to receive and retain a volume of curable material therein; and
curable material configured to be dispensed into the receptacle in a flowable form, wherein the curable material, once cured, is configured to bond to the retention member and to the medical device to immobilize the medical device relative to the retention member.

16. The system of claim 15, wherein the medical device comprises a therapy catheter.

17. The system of claim 15, wherein the medical device comprises a stimulation lead.

18. A method of implanting an elongate medical device through a burr hole, the method comprising:
securing a cranial anchor relative to the burr hole, the anchor comprising:
a base configured to secure to tissue surrounding the burr hole, the base comprising an upper side, lower side, outer edge, and inner edge, the inner edge defining an opening passing between the upper and lower sides; and
a cup-shaped retention member comprising a sidewall and a floor forming a partially enclosed receptacle having an open top, the receptacle configured to receive and retain a volume of curable material therein, the retention member removably received within the opening and secured to the base during implantation of the medical device, wherein the floor comprises a membrane operable to be pierced by the medical device, or by a tool used during implantation of the medical device;
aligning a guide cannula with a predetermined device trajectory through the burr hole;
inserting the guide cannula through the burr hole;
puncturing the membrane with the guide cannula;
inserting the medical device through the guide cannula;
withdrawing the guide cannula from the burr hole;
dispensing a volume of curable material into the retention member, wherein the volume of curable material is contained by the sidewall and floor; and
curing the volume of curable material to immobilize a portion of the medical device relative to the retention member.

* * * * *